United States Patent
Dozol et al.

(10) Patent No.: US 6,709,642 B1
(45) Date of Patent: Mar. 23, 2004

(54) CALIXARENE ACETAMIDO DERIVATIVES, PREPARATION AND USE THEREOF FOR EXTRACTING STRONTIUM

(75) Inventors: Jean-François Dozol, Pierrevert (FR); Rocco Ungaro, Parra (IT); Alessandro Casnati, Parra (IT)

(73) Assignee: Commissariat a l'Energie Atomiguie, Paris (FR)

( * ) Notice: Subject to any disclaimer, the term of this patent is extended or adjusted under 35 U.S.C. 154(b) by 195 days.

(21) Appl. No.: 10/049,493

(22) PCT Filed: Aug. 11, 2000

(86) PCT No.: PCT/FR00/02304

§ 371 (c)(1), (2), (4) Date: Feb. 12, 2002

(87) PCT Pub. No.: WO01/12586

PCT Pub. Date: Feb. 22, 2001

(30) Foreign Application Priority Data

Aug. 13, 1999 (FR) .............................................. 99 10480

(51) Int. Cl.[7] ........................ B01D 11/00; C07D 203/00
(52) U.S. Cl. ........................ 423/157; 436/79; 534/829; 534/831; 546/255; 546/266; 549/354; 558/400; 560/255
(58) Field of Search .......................... 423/157; 210/638, 210/643; 534/829, 831; 560/255; 558/400; 436/79; 546/255, 266; 564/251; 549/354

(56) References Cited

U.S. PATENT DOCUMENTS 5,043,415 A * 8/1991 Harris et al. ................. 528/205

(List continued on next page.)

FOREIGN PATENT DOCUMENTS

EP    0 309 291 A    3/1989

(List continued on next page.)

OTHER PUBLICATIONS

Chemistry Letters, pp. 947–948, XP000891490.

(List continued on next page.)

*Primary Examiner*—Stanley S. Silverman
*Assistant Examiner*—Maribel Medina
(74) *Attorney, Agent, or Firm*—Anderson Kill & Olick, PC.; Eugene Lieberstein; Michael N. Meller (57) ABSTRACT

The invention concerns derivatives of calixarene having the formula:

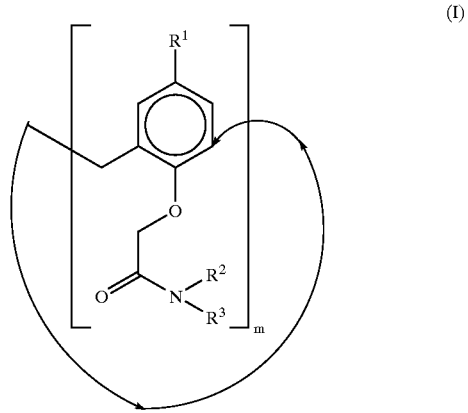

in which:

$R^1$ represents various hydrocarbon groups, $R^2$ and $R^3$ represent an alkyl, cycloalkyl or aryl group or a group having the formula: $O(CH_2)_n[O(CH_2)_p]_q OR^4$, or form a heterocyclic group with the nitrogen atom, and, n equals 6, 7 or 8.

These derivatives can be used for extracting strontium from aqueous solutions.

14 Claims, 4 Drawing Sheets

U.S. PATENT DOCUMENTS

| | | | |
|---|---|---|---|
| 5,210,216 A | * | 5/1993 | Harris et al. ............... 548/518 |
| 5,607,591 A | | 3/1997 | Dozol et al. |
| 5,926,687 A | | 7/1999 | Dozol et al. |

FOREIGN PATENT DOCUMENTS

| | | |
|---|---|---|
| EP | 0 432 989 | 6/1991 |
| JP | 08 127561 A | 5/1996 |
| WO | WO 94 12502 A | 6/1994 |
| WO | WO 94 24138 A | 10/1994 |
| WO | WO 97 17322 | 5/1997 |

OTHER PUBLICATIONS

Journal of the Chemical Society, Perkin Transactions 2, pp. 575–579, XP002133937.

Journal of the Chemical Society, Perkin Transactions 2, pp. 1063–1066, XP002133938.

Chemical Society of Japan, Bull Chem. Soc. Jpn., pp. 1499–1502 and American Chemical Society, Am. Chem. Soc. 1989, lll, pp. 8192–8200.

* cited by examiner

CALIXARENE ACETAMIDO DERIVATIVES, PREPARATION AND USE THEREOF FOR EXTRACTING STRONTIUM

TECHNICAL FIELD

The subject of the present invention is new derivatives of calixarenes carrying amide groups, their method of preparation and their use to extract strontium.

These new calixarene derivatives may be used to extract strontium present in aqueous solutions derived from reprocessing plants for spent nuclear fuel.

STATE OF PRIOR ART

The use of macrocyclic ligands such as calixarenes has already been considered to extract metals from aqueous solutions. Documents WO94/12502 [1] and WO94/24138 [2] describe crown-calixarenes which can be used for the selective extraction of caesium and actinides.

The extraction of caesium from aqueous solutions is of interest as caesium releases heat which hampers the storage of nitric solutions of fission products.

Strontium 90 is also an isotope giving major heat release, strontium and caesium accounting for more than 90% of the heat released from solutions of fission products.

Therefore, their removal from these solutions would facilitate the storage of such solutions. Also, the removal of caesium, strontium and actinides may make it possible to declassify type B waste so that it can be addressed to an existing surface storage rather than to a storage site under geological formation.

Solutions of this type may for example be evaporator concentrates or solutions generated by dismantling operations.

The subject of the present invention is precisely new derivatives of calixarenes.

DISCLOSURE OF THE INVENTION

The subject matter of the present invention is precisely new derivatives of calixarenes which lead to satisfactory extraction of strontium.

According to the invention, the new derivative of calixarene meets the formula:

(I)

in which:

$R^1$ represents a hydrogen atom, a hydroxyl, alkyl, alcoxy, aryl, aryloxy, arylalkyl, arylalcoxy, cycloalkyl or cycloalcoxy group, or a group having the formula $O(CH_2)_n[O(CH_2)_p]_qOR^4$ (II) in which $R^4$ represents a hydrogen atom or an alkyl group, n and p are whole numbers ranging from 1 to 6, and q equals 0 or is a whole number from 1 to 6, $R^2$ and $R^3$, which may identical or different, represent an alkyl, cycloalkyl or aryl group or a group having the formula: $O(CH_2)_n[O(CH_2)_p]_qOR^4$ (II) in which $R^4$, n, p and q are such as defined above, or $R^2$ and $R^3$, together with the nitrogen atom to which they are bound, form a heterocyclic group chosen from among the piperidyl, pyrrolidinyl, morpholinyl, thiomorpholinyl, tetrahydropyridyl, imidazolidinyl, indolinyl, tetrahydroquinolyl and perhydroindolyl groups, and m is a whole number ranging from 6 to 8.

In this formula, the alkyl and alcoxy groups may be linear or branched groups, preferably with 1 to 12 carbon atoms. The aryl and aryloxy groups which may be used are monovalent groups derived from an aromatic or heterocyclic core through removal of one hydrogen atom from one of the carbon atoms of the cycle.

By way of example of such groups, mention may be made of the phenyl, naphtyl, pyridyl, thiophenyl and substituted phenyl groups.

For $R^1$ it is also possible to use arylalkyl and arylalcoxy groups in which the alkyl or alcoxy group preferably has from 1 to 12 carbon atoms.

As an example of such groups, the benzyloxy group and the benzyl group may be cited.

When $R^1$ represents the group of formula (II), $R^4$ may be a hydrogen atom or a alkyl group preferably having from 1 to 12 carbon atoms.

According to the invention, $R^1$ is preferably an alkyl, alcoxy or arylalcoxy group, for example the tert-butyl group, the pentoxy or octoxy group, or the benzyloxy group.

According to the invention, $R^2$ and $R^3$ may be alkyl, cycloalkyl or aryl groups having from 1 to 12 carbon atoms.

Preferably, $R^2$ and $R^3$ are alkyl groups, the ethyl group for example.

The calixarenes may comprise from 6 to 8 phenyl cycles and the derivative preferably comprises 6 or 8 phenyl cycles, that is to say that m equals 6 or 8.

The calixarene derivatives of the invention may be prepared using methods that are easy to implement.

Therefore, if $R^1$ represents a hydrogen atom, an alkyl group or a benzyloxy group, the calixarene of formula (I) may be prepared in which $R^2$ and $R^3$ are such as defined above, using a method which comprises the reaction of a calixarene having the formula:

(III)

in which $R^1$ and m are as defined above, with a chloroacetamide having the formula:

(IV)

in which R² and R³ are such as defined above.

If, in the calixarene of formula (I) described above, R¹ represents an alcoxy group, this derivative of calixarene may be prepared using a method which comprises the following steps:

a) the reaction of a calixarene of formula:

(V)

in which m is such as defined above, with a chloroacetamide having the formula:

(IV)

in which R² and R³ are such as defined above, to obtain the derivative having the formula:

(VI)

in which R and R are such as defined above.

b) reaction of the derivative of formula (VI) with Pd(OH₂) to obtain the calixarene having the formula:

(VII)

c) reaction of the calixarene of formula VII with a halogenated derivative of formula R⁵X in which R⁵ represents an alkyl group and X is a halogen atom, to obtain the calixarene derivative of formula (I) in which R¹ represents the alcoxy group OR⁵.

The calixarenes of formula (III) used as starting products for the preparation of the derivatives of the invention may be prepared by condensation reaction of p-benzyloxyphenol having the formula:

(VIII)

to obtain a mixture of calix[6]arene, calix[7]arene and calix[8]arene of formula (III), and separation of the calixarene of formula (III) in which m=6 or 8.

The calixarenes of formula (I) of the invention may be used to extract the strontium present in an aqueous solution, in particular an acid or saline solution derived from reprocessing plants for spent nuclear fuel.

The calixarenes of the invention which contain an acetamido group in which the amido group is a tertiary amide group (R1 and R2 being alkyl groups), are much more efficient and much more selective towards strontium than calixarenes which have a secondary amide group (R1=H, R2=alkyl) or a primary amide group (R1=R2=H).

In addition, the presence of the hydroxy, alcoxy, aryloxy, arylalcoxy or cycloalcoxy groups on the phenyl cores of calixarene makes them even more selective towards strontium. It has been observed that calixarenes using alkyl groups do extract strontium but less so than sodium.

The method of extraction of the invention is intended in particular for the extraction of strontium in low concentration, $5.10^{-4}$ M for example, from media containing 4 moles of sodium per litre.

Calixarenes with alkyl substitutes cannot therefore be used in this case since they extract sodium more than strontium.

Moreover, the calixarenes of the invention containing 6, 7 or 8 phenyl cores are more efficient than the calix[4]arenas or the calix[5]arenas for the extraction of strontium in the presence of sodium.

To conduct extraction of strontium, in accordance with the invention, the aqueous solution containing the strontium to be separated is placed in contact with an immiscible phase containing at least one derivative of calixarene meeting formula (I) given above, to extract the strontium in the immiscible phase.

This immiscible phase is generally made up of a solution of the calixarene or calixarenes of the invention in an appropriate organic solvent.

By way of example of solvents which may be used, mention may be made of alkyl benzenes and nitrophenyl alkyl ethers.

Preferably, an ether is used as solvent, such as ortho-nitrophenyl hexyl ether.

The calixarene concentration of the immiscible liquid phase depends in particular upon the solvent used. Concentrations ranging from $10^{-4}$ to $5.10^{-2}$ mol/L may be used, for example a concentration of $10^{-2}$ mol/L.

To implement the extraction method of the invention, the contacting of the aqueous solution with this immiscible liquid phase may be made in conventional liquid-liquid extraction installations, such as mixers-decanters, centrifugal extractors, pulsed columns etc.

The invention may be used to extract strontium from aqueous solutions, from nitric solutions in rparticular having a nitric acid concentration of 1 to 4 mol/L, and to extract strontium from solutions with high salinity, for example with sodium nitrate concentrations of 1 to 4 mol/L.

It can be used in particular to extract strontium from solutions with a very low strontium concentration relative to the sodium concentration of these solutions.

Other characteristics and advantages of the invention will become better apparent on reading the following example, evidently given for illustration purposes only and are non-restrictive, with reference to the appended drawings.

DETAILED DESCRIPTION OF EMBODIMENTS

The following examples illustrate the preparation of calixarene derivatives according to the invention.

Figure 1:
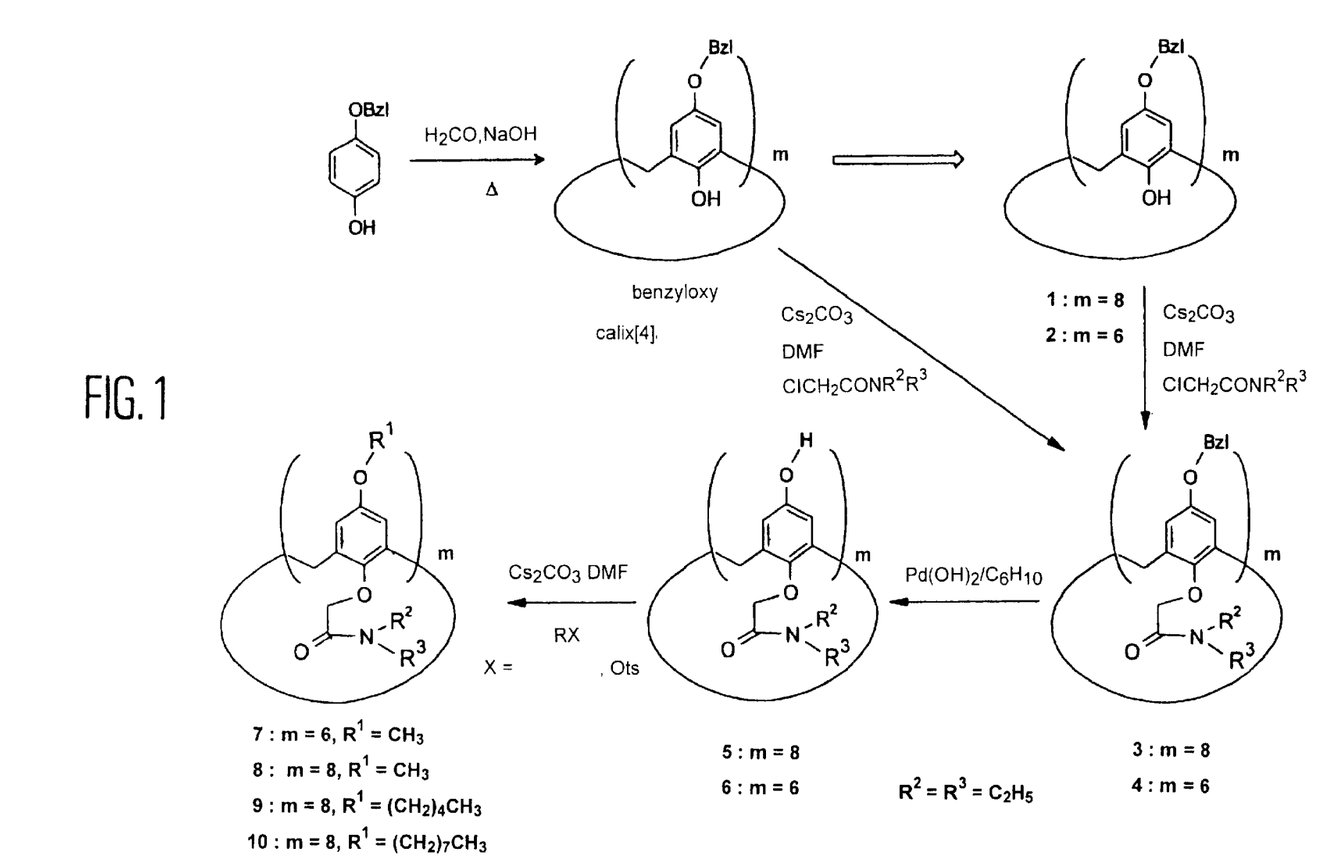
FIG. 1 is a summary diagram of the calixarenes of formula (I) corresponding to examples 1 to 10.

The summary diagram of examples 1 to 11 is given in FIG. 1 (compounds 1 to 10).

EXAMPLE 1

Preparation of a Mixture of P-benzyloxycalix[n] arenas in Which m Equals 6, 7 and 8

20.0 g (0.1 mol) of p-benzyloxyphenol are dissolved in 400 ml xylene in a round-bottomed 1 litre flask fitted with the water collector of DEAN & STARK type. The solution is heated to 100° C., then 1.1 ml (2 mmol) of an aqueous 2N NaOH solution are added and 5.4 g (179.8 mmol) of paraformaldehyde. After 2 hours, the temperature is raised to 150° C. and a precipitate starts to form. The reaction mixture is refluxed for 48 hours, and it is then cooled and filtered on a Buchner funnel, which gives a solid corresponding to the mixture of p-benzyloxycalix(nlarenes in which m equals 6, 7 and 8.

EXAMPLE 2

Preparation of 5,11,17,23,29,35,41,47-octabenzyloxy-49,50,51,52,53,54,55,56-octa-hydroxycalix[8]arene (Compound 1)

The product resulting from the condensation reaction obtained in example 1 is washed in diethyl ether, and it is then transferred to a round-bottomed 250 ml flask and placed in suspension in 200 ml methylene chloride. The heterogeneous solution is refluxed for 3 hours, and it is then hot filtered through a Bucher funnel. 10.2 g of a white product is obtained, formed of compound 1, i.e. a yield of 48%.

The characteristics of compound 1 are the following:

Melting point: above 300° C.; $^1H$ NMR (DMSO-$D_6$): δ=8.63 (s, 8H, OH), 7.29 (s, 4OH, PhH, 6.60 (s, 16H, ArH), 4.80 (S, 16H, $OCH_2Ph$), 3.80 (s, 16H, $ArCH_2Ar$); $^{13}C$ NMR (DMSO-$D_6$): δ=151.0 (s, Ar ipso), 146.6 (s, Ar para), 137.6 (s, Ph), 128.9 (s, Ar ortho), 128.1 127.6 (d, Ph), 114.1 (d, AR meta), 69.7 (t, $OCH_2Ph$), 32.0 (t, $ArCH_2Ar$); MS (CI$^-$) 1696 (M$^+$); Analysis calculated for $C_{112}H_{96}O_{16}$: C, 79.23; H, 5.69. Finding: C, 79.11; H, 5.80.

EXAMPLE 3

Preparation of 5,11,17,23,29,35-Hexa-benzyloxy-37,38,39,40,41,42-hexahydroxycalix[6] arene (Compound 2)

The precipitation mother liquor of compound 1 obtained in example 2 is used, and the dichloromethane is removed by distilling. The residue is treated with 50 ml ethyl ether. The formed precipitate is filtered through a Buchner funnel. 1.1 g of compound 2 is obtained, which corresponds to a yield of 5%.

The characteristics of compound 2 are as follows:

Melting point: above 300° C.; $^1H$ NMR (DMSO-$D_6$, 300K); δ=8.52 (s, 6H, OH), 7.29 (m, 30H, PhH), 6.64 (s, 12H, ArH), 4.83 (s, 12H, $CH_2Ph$), 3.75 (s, 12H, $ArCH_2Ar$); $^{13}C$ NMR DMSO-$D_6$, 300K); δ=151.7 (s, Ar ipso), 144.9 (s, Ar para), 137.2 (s, Ph), 128.6 (s, Ar ortho), 128.5, 128.1, 127.6 (d, Ph), 114.3 (d, Ar meta), 69.3 (t, $OCH_2Ph$), 31.2 (t, $ArCH_2Ar$). MS (CI$^+$) 1273.4 (M+H$^+$); Analysis calculated for $C_{84}H_{72}O_{12}$: C, 79.23; H, 5.69. Finding: C, 79.18; H, 5.77.

EXAMPLE 4

Preparation of 5,11,17,23,29,35,41,47-Octabenzyloxy-49,50,51,52,53,54,55,56-octakis[(N, N-diethylamino-carbonyl)methoxy]calix[8]arene: (Compound 3)

The starting product is a solution containing 0.40 mmol of compound 1 dissolved in 20 ml dry DMF dimethylformamide which is heated to 90° C. under stirring with $Cs_2CO_3$ (4 moles per each OH mole) and 6 moles for each OH mole of α-chlorodiethylacetamide.

After 15 to 20 hours, to the cooled reaction mixture are added 75 ml 1N HCl and the crude product is filtered through a Buchner funnel and washed in water.

The solid is dissolved in 20 ml $CH_2Cl_2$ and the organic solution is washed in 2×25 ml 2N HCl and 2×25 ml water. The organic phase is dried on $MgSO_4$, the dichloromethane is removed by distillation and the product obtained is purified by crystallisation using $CH_2Cl_2/CH_3OH$ at −10° C. Compound 3 is obtained with a yield of 61%.

The characteristics of compound 3 are the following:

Melting point: above 300° C.; $^1H$ NMR ($CDCl_3$); δ=7.13 (m, 40H, PhH), 6.54 (s, 16H, ArH), 4.54 (s, 16H, $OCH_2Ph$), 4.42 (s, 16H, $OCH_2CO$), 4.04, (s, 16H, $ArHCH_2Ar$), 3.25 (q, J=7 Hz, 16H, $NCH_2CH_3$)), 3.12 (q, J=7 Hz, 16H, $NCH_2CH_3$) 0.99 (t, J=7 Hz, 24H, $NCH_2CH_3$) 0.93 (t, J=7 Hz, 24H, $NCH_2CH_3$); $^{13}C$ NMR $CDCl_3$: δ=166.9 (s, $OCH_2CO$), 155.0 (s, Ar ipso), 149.2 (s, Ar para), 137.0 (s, Ph), 128.0 (s, Ar ortho), 127.5, 127.4 (d, Ph), 115.0 (d, Ar meta), 72.1 (t, $OCH_2CO$), 69.4 (t, $OCH_2Ph$), 41.1, 39.9 (t, $NCH_2CH_3$) 30.5 (t, $ArCH_2Ar$), 14.1, 12.7 (q, $NCH_2CH_3$); MS (FAB) m/z 2601 ($M^+$). Analysis calculated for: $C_{160}H_{184}O_{24}N_8$: C, 73.83; H, 7.12, N, 4.30. Finding: C, 73.71; H, 7.19; N, 4.48.

EXAMPLE 5

Preparation of 5,11,17,23,29,35-Hexabenzyloxy-37-38,39,40,41,41-hexakis[N,N-diethyl-aminocarbonyl)methoxy]calix[6]arene (Compound 4)

The same operating mode is followed as for example 4, to prepare compound 4 from compound 2.

The product obtained is purified by crystallization under the same conditions and compound 4 is obtained with a yield of 75%.

The characteristics of compound 4 are as follows:

Melting point: 246–247° C.; $^1H$ NMR ($CDCl_3$, 300K): δ=7.52–7.11, 6.81, 6.80, 6.19 and 5.97 (42H, PhH and ArH), 5.07–4.23 (m, 27H, $OCH_2Ph$, $OCH_2CO$, $ArCH_2Ar$), 3.96, 3.79, 3.40 (bs, 25H, $NCH_2CH_3$, $ArCH_2Ar$), 3.08, 2.49 (q, 2H, each $NCH_2CH_3$), 1.86 (bs, 30H, $NCH_2CH_3$), 0.75 and −0.51 (t, 3H each $NCH_2CH_3$), 0.90, 0.70, −0.19, −1.61 (bs, 1H, $NCH_2CH_3$); $^1H$ NMR (DMSO-$d_6$, 373K): δ=7.31 and 7.24 (s, 30H, PhH), 6.88 (bs, 12H, ArH), 4.88 (s, 12H, $OCH_2Ph$, 4.45 (s, 12H, $OCH_2CO$), 3.91 (bs, 12H, $ArCH_2Ar$), 3.26 (bs, 24H, $NCH_2CH_3$, 1.01 (bs 36H, $NCH_2CH_3$), $^{13}C$ NMR ($CDCl_3$, 300K): δ=168.0, 167.6, 167.5, 167.3, 166.9 (s, $OCH_2CO$), 155.1, 154.9, 154.3, (s, Ar ipso), 151.4, 150.7, 148.9, (s, Ar para), 138.1, 137.6, 137.1 (s, Ph), 135.4, 134.8, 134.5, (s, Ar ortho), 133.7, 133.5, 128.5, 128.1, 127.9, 127.4, 127.1, 126.9 (d, Ph), 117.4, 116.9, 116.5, 116.0, 115.3, 113.8, 113.5 (d, Ar meta), 74.7, 72.5, 71.4, 70.3, 69.8, 69.2 (t, $OCH_2CO$), 41.62, 41.42, 41.0, 41.0, 40.1, 39.5 (t, $NCH_2CH_3$), 32.5, 32.1, 31.1 (t, $ArCH_2Ar$), 14.5, 12.9, 12.3, 12.1 (q, $NCH_2CH_3$). Analysis calculated for $C_{120}H_{138}O_6N_{18}$: C, 73.82; H, 7.12; N, 4.30. Finding: C, 73.78; H, 7.18; N, 4.39. MS (CI): 1952 $(M+1)^+$.

EXAMPLE 6

Preparation of 5,11, 17, 23, 29, 35, 41, 47-Octahydroxy-49,50,51,52,53,54,55,56-octakis[N,N-diethylaminocarbonyl)methoxy]calix[8]arene (Compound 5)

0.5 g of compound 3 obtained in example 4 are placed in suspension in a mixture of 10 ml ethanol and 9 ml cyclohexene in a Schlenk tube under nitrogen. After adding 0.1 g (20% w/w relative to calixarene) $Pd(OH)_2/C$ (20%, Pearlman catalyst), the reaction mixture is heated to 90° C. for 15 to 18 hours. The catalyst is then removed by filtration on a Celite filter, the filter is carefully washed with $CH_2Cl_2$, $C_2H_5OH$ and again with $CH_2Cl_2$.

The collected filtrates are evaporated in a vacuum to dryness, which gives a crude product with a quantitative yield of more than 90%. The crude product may be crystallized using hexane and compound 5 is thus obtained with a yield of 90%.

The characteristics of compound 5 are the following:

Melting point: above 300° C.; $^1H$ NMR ($CDCl_3/CD_3OD=$ 3/1): δ=6.38 (s, 16H, ArH), 4.41 (s, 16H, $OCH_2Ph$), 3.93, (s, 16H, $ArCH2Ar$), 3.16 (d, J=7 Hz, 16H, $NCH_2CH_3$, 3.13 (d, J=7 Hz, 16H, $NCH_2CH_3$) $NCH_2CH_3$) 1.04 (t, J=7 Hz, 24H, $NCH_2CH_3$) 0.94 (t, J=7 Hz, 24H, $NCH_2CH_3$), $^{13}C$ NMR ($CDCl_3$): $CD_3OD$=3:1): δ=168.7 (s, $OCH_2CO$), 153.9 (s, Ar ipso), 148.6 (s, Ar para), 135.3 (s, Ar ortho), 116.1 (d, Ar meta), 72.0 (t, $OCH_2CO$), 42.1, 41.0 (t, $NCH_2CH_3$), 30.9 (t$ArCH_2Ar$), 14.2 12.9 (q, $NCH_2CH_3$), MS ($FAB^+$) m/z 1880.7 ($M^+$); Analysis calculated for $C_{104}H_{136}O_{24}N_8$: C, 66.37; H, 7.27; N; 5.95. Finding: C, 66.45; H, 7.39; N, 6.07.

EXAMPLE 7

Preparation of 5,11,17,23,29,35-Hexahydroxy-37, 38,39,40,41,42-hexakis[N,N-diethylaminocarbonyl)-methoxy]calix[6]arene (Compound 6)

In this example, the same operating mode is followed as in example 6 to prepare compound 6 from compound 4.

Compound 6 is obtained with a yield of 80%.

The characteristics of compound 6 are the following:

Melting point: 255° C. (decomposed); $^1H$ NMR (DMSO-$d_6$, 300K): δ=8.3 (bs, 6H, ArOH), 6.6 (bs, 12H, ArH), 4.21 (bs, 12H, $OCH_2CO$), 3.85 (bs, 12H, $ArCH_2Ar$) 3.30 (bs, 24H, $NCH_2CH_3$), 1.0 (bs, 36H, $NCH_2CH_3$), $^1H$ NMR (DMSO-$d_6$, 343K); δ=8.11 (s, 6H, ArOH), 6.35 (s, 12H, ArH), 4.35 (s, 12H, $OCH_2CO$), 3.81, (s, 12H, $ArCH_2Ar$) 3.20 (bs, 24H, $NCH_2CH_3$), 0.90 (bs, 36H, $NCH_2CH_3$), $^{13}C$ NMR ($CDCl_3$): d=166.8 (s, $OCH_2CO$), 152.5 (s, Ar ipso), 147.8 (s, Ar para), 113.6 (s, Ar ortho), 115.8 (d, Ar meta), 79.4 (t, $OCH_2CO$), 40.71 (t, $NCH_2CH_3$), 30.3 (t, $ArCH_2Ar$), 13.7, 12.6 (q, $NCH_2CH_3$), MS (FAB+) m/z 1410.9 ($M^+$). Analysis calculated for $C_{78}H_{102}O_6N_{18}$: C, 66.36; H, 7.28; N, 5.95. Finding: C, 66.44; H, 7.33; N, 6.02.

EXAMPLE 8

Preparation of 5,11,17,23,29,35-Hexamethoxy-37, 38,39,40,41,42-hexakis[N,N-diethylaminocarbonyl)-methoxy]calyx[6]arene (Compound 7)

To a stirred solution of 0.5 mmol of compound 6 dissolved in 80 ml dry DMF are added 3 moles $Cs_2CO_3$ for each OH mole and iodomethane to the proportion of 3 mol per OH mole. The reaction mixture is heated to 90° C., in a nitrogen atmosphere, for 18 hours. The DMF is then removed under reduced pressure and the residue is cooled with 75 ml 10% HCl aqueous solution. 75 ml dichloromethane are added, the organic layer is separated and washed twice in 50 ml water. The organic phase is dried on $MgSO_4$ and the solvent is removed under reduced pressure.

Compound 7 is obtained with a yield of 95%.

The characteristics of compound 7 are the following:

Melting point: 108–110° C.; $^1H$ NMR (DMSO-$D_6$, 300K): δ=7.3–6.8 and 5.7 (bs, 12H, ArH), 4.63 (bs, 12H, OCH$_2$CO), 4.3 (bs, 12H, ArCH$_2$Ar), 3.9–3.4 (bs, 42H, OCH$_3$ and NCH$_2$CH$_3$), 1.10 (bs, 36H, NCH$_2$CH$_3$), $^1$H NMR (DMSO-d$_6$, 343K): d=6.70 (s, 12H, ArH), 4.43 (s, 12H, OCH$_2$CO), 3.85 (s, 12H, ArCH$_2$Ar), 3.54 (s, 18H, OCH$_3$), 3.17 (bs, 24H, NCH$_2$CH$_3$), 0.96 (bs, 36H, NCH$_2$CH$_3$); $^{13}$C NMR (CDCl$_3$, 300K): δ=167.1, 166.7 (s, OCH$_2$CO), 155.9, 155.8 (s, Ar ipso), 148.5, 148.3 (s, Ar para), 136.2, 135.3, 135.1, 134.5, 134.2 (s, Ar ortho), 116.6, 116.0, 115.7, 114.8, 114.6, 113.9 (d, Ar meta), 72.4, 72.2 (t, OCH$_2$CO), 57.4, 56.8, 55.3 (q, OCH$_3$), 41.2, 39.9 (t, NCH$_2$CH$_3$), 31.7 (t, ArCH$_2$Ar), 14.5, 12.8 (q, NCH$_2$CH$_3$). Analysis calculated for C$_{84}$H$_{114}$N$_6$O$_{18}$: C, 67.44; H, 7.68; N, 5.62. Finding: C, 67.38; H, 7.75; N, 5.73. MS (CI+)=1496 (M+H$^+$).

EXAMPLE 9

Preparation of 5,11,17,23,29,35,41,47-Octamethoxy-49,50,51,52,53,54,55,56-octakis[(N,N-diethylaminocarbonyl)methoxy]calix[8]arene (Compound 8)

The same operating mode is followed as for example 8 to prepare compound 8 from compound 5 also using iodomethane CH$_3$I.

Compound 8 is obtained with a yield of 70%.

The characteristics of this compound are as follows:

Melting point: 96–97° C.; $^1$H NMR CDCl$_3$: δ=6.43 (s, 16H, ArH), 4.43 (s, 16H, OCH$_2$CO), 4.04 (s, 16H, ArCH$_2$Ar), 3.45 (s, 24H, OCH$_3$) 3.29 (d, 16H, NCH$_2$CH$_3$), J=6.3 Hz), 3.13 (d, 16H, NCH$_2$CH$_3$), J=6.3 Hz), 1.04 (t, 24H, NCH$_2$CH$_3$), J=6 Hz), 0.90 (t, 24H, NCH$_2$CH$_3$ J=6 Hz). $^{13}$C NMR (CDCl$_3$, 300K): δ=166.9 (s, OCH$_2$CO), 155.9, (s, Ar ipso), 148.9 (s, Ar para), 134.6 (s, Ar ortho), 113.9 (d, Ar meta), 72.0 (t, OCH$_2$CO), 54.9 (s, OCH$_3$), 41.0, 39.8 (t, NCH$_2$CH$_3$) 30.5 (t, ArCH$_2$Ar), 14.0, 12.6 (q, NCH$_2$CH$_3$). Analysis calculated for C$_{112}$H$_{152}$N$_8$O$_{24}$: C, 67.45; H, 7.68; N, 5.62. Finding: C, 67.54; H, 7.56; N, 5.77. MS (CI+): m/z=1994 (M+H$^+$).

EXAMPLE 10

Preparation of 5,11,17,23,29,35,41,47-Octapentoxy-49,50,51,52,53,54,55,56-ocatkis[N,N-diethylaminocarbonyl)methoxy]calix[8]arene (Compound 9)

The same operating mode is followed as for example 8 to prepare compound 9 from compound 5, using n—CH$_3$(CH$_2$)$_4$I as alkylation agent.

Pure compound 9 is obtained by flash chromatography (SiO$_2$: AcOEt/MeOH=10/1) with a yield of 65%.

The characteristics of this compound are as follows: $^1$H NMR CDCl$_3$: δ=6.49 (s, 16H, ArH), 4.37 (s, 16H, OCH$_2$CO), 4.00 (s, 16H, ArCH$_2$Ar), 3.65 (bs, 16H, OCH$_2$R) 3.24 (bs, 16H, NCH$_2$CH$_3$), 3.11 (bs, 16H, NCH$_2$CH$_3$), 1.55 (bs, 48H, (CH$_2$)$_3$), 1.28 (bs, 24H, RCH$_3$), 1.01 (t, 24H, NCH$_2$CH$_3$, 0.85 (t, 24H, NCH$_2$CH$_3$). $^{13}$C NMR (CDCl$_3$): δ=166.9 (s, OCH$_2$CO), 155.3, (s, Ar ipso), 148.9 (s, Ar para), 134.3 (s, Ar ortho), 114.6 (d, Ar meta), 72.1 (t, OCH$_2$CO), 67.7 (s, OCH$_2$R), 41.0, 39.8 (t, NCH$_2$CH$_3$) 30.4 (t, ArCH$_2$Ar), 28.8 (t, CH$_2$CH$_2$CH$_2$CH$_3$), 28.7 (t, CH$_2$CH$_2$CH$_3$), 22.3 (t, CH$_2$CH$_3$), 13.8 (q, CH$_3$), 14.0, 12.6 (q, NCH$_2$CH$_3$). Analysis calculated for C$_{144}$H$_{216}$N$_8$O$_{24}$: C, 70.79; H, 8.91; N, 4.59. Finding: C, 70.83; H, 8.86; N, 4.66. MS (CI+): m/z=2443 (M+H)$^+$.

EXAMPLE 11

Preparation of 5,11,17,23,29,35,41,47-Octaoctoxy-49,50,51,52,53,54,55,56-octakis[N,N-diethylaminocarbonyl)methoxy]calix[8]arene (Compound 10)

In this example the same operating mode is followed as in example 8 using compound 5 and using n—CH$_2$3(CH$_2$)$_7$ Ots as alkylation agent.

Compound 10 is obtained in the pure state by flash chromatography (SiO$_2$: AcOEt/MeOH=10/0.1), with a yield of 57%.

The characteristics of compound 10 are the following.

Melting point: 68–70° C.; $^1$H NMR CDCl$_3$: δ=6.47 (bs, 16H, ArH), 4.34 (bs, 16H, OCH$_2$CO), 3.99 (s, 16H, ArCH$_2$Ar), 3.65 (bs, 16H, OCH$_2$R) 3.22 (bs, 32H, NCH$_2$CH$_3$), 1.23 (bs, 96H, (CH$_2$)$_6$CH$_3$), 0.90 (bs, 24H, NCH$_2$CH$_3$), 0.86 (bs, 24H, NCH$_2$CH$_3$), 0.83 (t, J=6.5 Hz, 24H, (CH$_2$)$_7$CH$_3$). 13C NMR (CDCl$_3$): δ=166.9 (s, OCH$_2$CO), 155.2, (s, Ar ipso), 148.9 (s, Ar para), 134.4 (s, Ar ortho), 114.6 (d, Ar meta), 72.0 (t, OCH$_2$CO), 67.7 (s, OCH$_2$R), 41.0, 39.8 (t, NCH$_2$CH$_3$) 31.7 (t, CH$_2$CH$_2$CH$_2$CH$_2$CH$_2$CH$_3$) 30.4 (t, ArCH$_2$Ar), 29.5 (t, CH$_2$CH$_2$CH$_2$CH$_2$CH$_3$), 22.4 (t, CH$_2$CH$_3$) 13.8 (q, CH$_3$), 14.0, 12.6 (q, NCH$_2$CH$_3$). Analysis calculated for C$_{168}$H$_{264}$N$_8$O$_{24}$: C, 72.58; H, 9.57; N, 4.03. Finding: C, 72.62; H, 9.51; N, 4.12. MS (CI+): m/z=27779 (M+1)$^+$.

Figure 2:
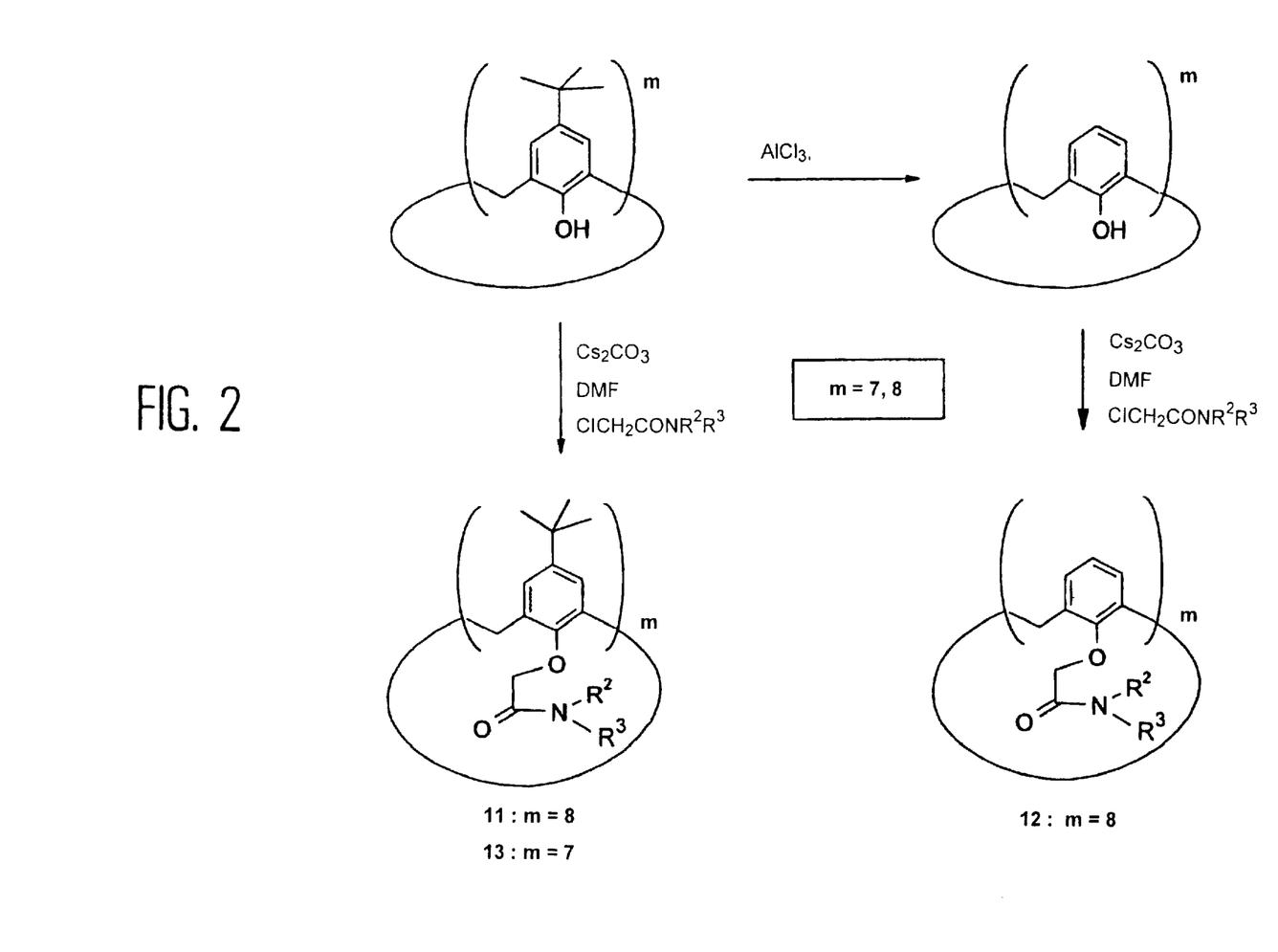
FIG. 2 is a summary diagram of the calixarenes of formula (1) corresponding to examples 11 to 13.

The summary diagram of examples 12 to 14 is illustrated in FIG. 2.

EXAMPLE 12

Preparation of 5,11,17,23,29,35,41,47-Octakis (1,1-dimethylethyl)-49,50,51,52,53,54,55,56-octakis [N, N-diethylaminocarbonyl)methoxy]calix[8]arene (Compound 11)

In this example, the same operating mode is followed as in example 4 to prepare compound 11 from 5,11,17,23,29, 35,41,47-octakis(1,1-dimethylethyl)calyx[8]arene, that is to say the compound of formula (III) in which R represents the tert-butyl group and m equals 8.

Compound 11 is thus obtained in the pure state by crystallization using methanol, with a yield of 64%.

The characteristics of compound 11 are as follows:

Melting point: above 300° C.; $^1$H NMR CDCl$_3$: δ=6.69 (bs, 16H, ArH), 4.37 (s, 16H, OCH$_2$CO), 4.13 (s, 16H, ArCH$_2$Ar), 3.21 (bs, 16H, NCH$_2$CH$_3$) 1.05 (s, 72H, tBu), 1.22 (t, 24H, J=7 Hz, NCH$_2$CH$_3$), 0.84 (t, 24H, J=7 Hz, NCH$_2$CH$_3$). $^{13}$C NMR (CDCl$_3$): δ=167.0 (s, OCH$_2$CO), 153.4 (s, Ar ipso), 146.0 (s, Ar para), 132.5 (s, Ar ortho), 125.9 (d, Ar meta), 71.1 (t, OCH$_2$CO), 41.1, 39.9 (t, NCH$_2$CH$_3$) 34.1 (s, C(CH$_3$)$_3$), 31.2 (t, ArCH$_2$Ar), 31.4 (s, C(CH$_3$)$_3$), 14.0, 12.8 (q, NCH$_2$CH$_3$). Analysis calculated for C$_{136}$H$_{200}$N$_8$O$_{16}$: C, 74.14; H, 9.15; N, 5.09. Finding: C, 74.03; H, 9.22; N, 5.18. MS (CI+)=2201 (M$^+$).

EXAMPLE

Preparation of 49,50,51,52,53,54,55,56-Octakis[N, N-diethylaminocarbonyl)methoxy]calix[8]arene (Compound 12)

The same operating mode is followed as in example 4 to prepare compound 12 from calix[8]arene. The pure compound 12 is obtained by flash chromatography (SiO$_2$, AcOEt/MET$_3$=10/0.5) and crystallization using cold ethyl acetate, with a yield of 75%.

The characteristics of compound 12 are the following:

Melting point: 84–86° C.; $^1$H NMR CDCl$_3$: δ=6.61 (bs, 16H, ArH), 4.40 (s, 16H, OCH$_2$CO), 4.10 (s, 16H, ArCH$_2$Ar), 3.31–3.01 (m, 32H, NCH$_2$CH$_3$), 1.10–0.77 (m, 48H, NCH$_2$CH$_3$), $^{13}$C NMR (CDCl$_3$): δ=166.8 (s, OCH$_2$CO), 155.4 (s, Ar ipso), 133.8 (s, Ar ortho), 129.0 (d, Ar meta), 124.3 (d, Ar para), 71.5 (t, OCH$_2$CO), 40.9, 39.7 (t, NCH$_2$CH$_3$) 30.4 (t, ArCH$_2$Ar), 13.9, 12.7 (q, NCH$_2$CH$_3$).

Analysis calculated for $C_{104}H_{136}N_8O_{16}$: C, 71.20; H, 7.81; N, 6.39. Finding: C, 71.15; H, 7.79; N, 6.44. MS (CI)=1753 $(M)^+$.

EXAMPLE 14

Preparation of 5,11,17,23,29,35,41-Heptakis(1,1-dimethylethyl)-43,44,45,46,47,48,49-heptakis[N,N-diethylaminocarbonyl)methoxy]calix[7]arene (Compound 13)

Compound 13 is obtained following the same operating mode as in example 4 using 5,11,17,23,29,35,41-heptakis (1,1-dimethylethyl)calix[7]arene.

This calixarene was prepared using the method described by Shinkai, Bull. Chem. Soc. Jpn, 1994, 10499 [3]; Markoxitz JACS, 1989, 111, 81–92 [4].

Compound 13 is obtained in the pure state by crystallization using methanol, with a yield of 70%.

The characteristics of this compound are the following:

Melting point: above 248–250° C. $^1H$ NMR $CDCl_3$: $\delta$=7.03 (s, 14H, ArH), 4.48 (s, 14H, $OCH_2CO$), 4.04 (s, 14H, $ArCH_2Ar$), 3.38–3.23 (m, 28H, $NCH_2CH_3$) 1.03 (s, 63H, tBu), 1.00 (t, 42H, J=7 Hz, $NCH_2CH_3$). $^{13}C$ NMR ($CDCl_3$): $\delta$=167.2 (s, $OCH_2CO$), 153.4 (s, Ar ipso), 147.1 (s, Ar para), 132.6 (s, Ar ortho), 126.4 (d, Ar meta), 72.1 (t, $OCH_2CO$), 40.1, 39.9 (t, $NCH_2CH_3$) 34.0 (s, $C(CH_3)_3$), 31.4 (s, $C(CH_3)_3$), 31.2 (t, $ArCH_2Ar$), 14.5, 12.9 (q, $NCH_2CH_3$). Analysis calculated for $C_{119}H_{175}N_7O_{14}$: C, 74.14; H, 9.15; N, 5.09. Finding: C, 74.07; H, 9.20; N, 5.13. MS (CI+): 1926.8 $(M^+)$.

EXAMPLE 15

In this example, the efficacy of the compounds of the invention is tested to extract the following M metals: caesium-137, strontium-85 and sodium-22, from an aqueous nitric solution having a nitric acid concentration of 1M and containing $5.10^{-4}$ M of metals M to be extracted.

In this example, 3 ml of each aqueous solution containing only one of the metals to be extracted is contacted with 3 ml of an organic solution made up of nitrophenyl hexylether (NPHE) containing $10^{-2}$ mol/L of the tested calixarene. Contact is made in a 20 ml polypropylene tube which is shaken.

After a contact time of 1 hour, the two phases are left to settle and their respective contents of sodium, strontium and caesium are measured.

The distribution coefficient $D_M$ is then determined corresponding to the ratio of the concentration of element M in the organic phase over the concentration of this same element M in the aqueous phase.

The results obtained and the tested calixarenes are given in table 1.

EXAMPLE 16

In this example, the extracting properties of the calixarenes of the invention are tested vis-à-vis cobalt-60, strontium-85, caesium-137 and europium-152 present in an aqueous solution containing $10^{-2}$ mol/L $HNO_3$ and 4 mol/L $NaNO_3$. The same operating mode is followed as in example 15 to assure extraction of the compounds listed in table 2 whose concentration in NPHE is $10^{-2}$ mol/L.

The results obtained are given in table 2.

EXAMPLE 17

In this example, the efficacy of the calixarenes of the invention is tested to extract $^{60}Co$, $^{85}Sr$, $^{137}Cs$ and $^{152}Eu$ from an aqueous solution having a nitric acid concentration of 1 mol/L and containing 4 mol/L $NaNO_3$.

The operating mode is identical to the one in example 15, and the results obtained and the calixarenes used are given in table 3.

EXAMPLE 18

In this example, the efficacy of the calixarene (compound 10) is tested to extract strontium from nitric aqueous solutions having variable concentrations ($10^{-3}$, $10^{-2}$, $10^{-1}$, and 10 M) in nitric acid.

The same operating mode is followed as in example 15 with compound 10 at a concentration of $10^{-2}$ mol/L in NPHE.

Figure 3:
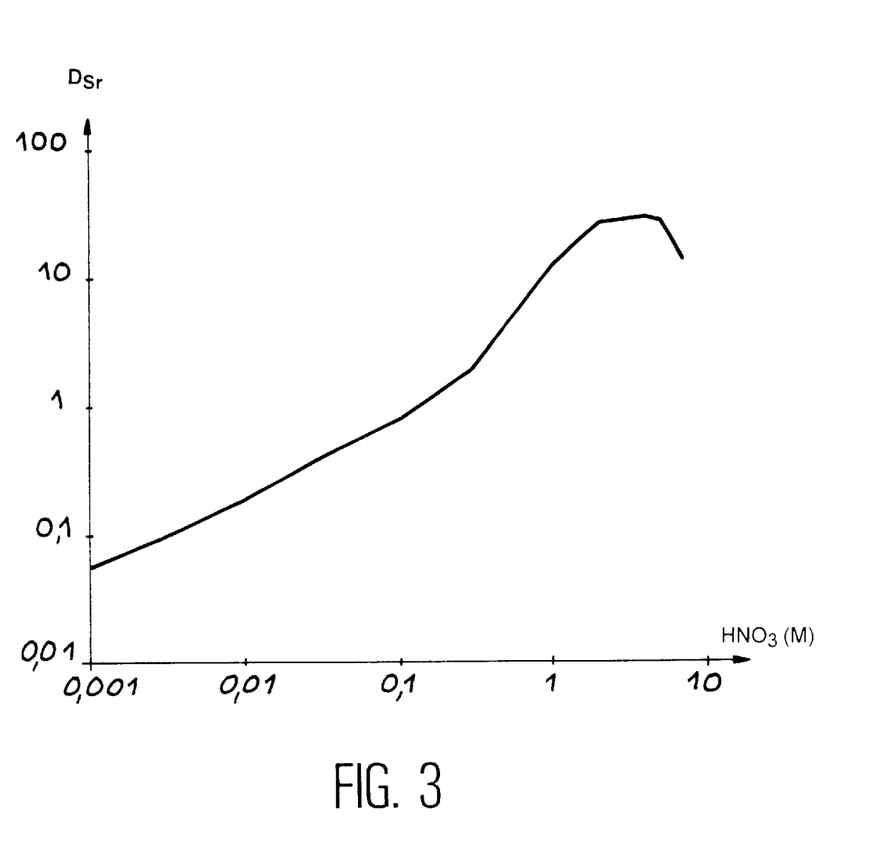
FIG. 3 illustrates the changes in the coefficient of distribution $D_{Sr}$ in relation to the nitric acid concentration of the initial solution (in mol/L) in the case of compound 10.

The results obtained are given in FIG. 3 which illustrates the changes in the distribution coefficient $D_{Sr}$ in relation to the nitric acid concentration.

EXAMPLE 19

In this example, the efficacy of the calixarene (compound 10) is tested to extract strontium and sodium from aqueous solutions with a nitric acid concentration of 1 M and variable $NO_3Na$ concentrations (0.5, 1, 2, 3 and 4 M). The same operating mode is followed as in example 15 using an organic phase made up of compound 10 at a concentration of $10^{-2}$ mol/L in NPHE.

Figure 4:
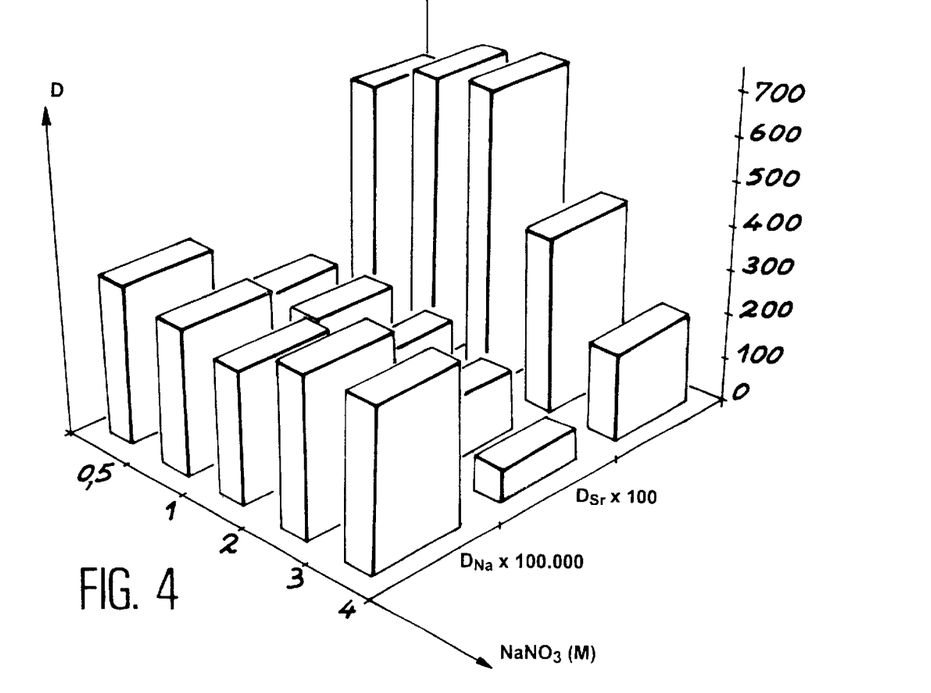
FIG. 4 illustrates the changes in the distribution coefficients $D_{Sr}$ and $D_{Na}$ and in Sr/Na selectivity in relation to the sodium nitrate content of the initial solution (in mol/L) and for a constant $HNO_3$ content of 1M.

The results obtained are given in FIG. 4 which illustrates the changes in $D_{Sr}$, $D_{Na}$ and Sr/Na selectivity in relation to the concentration of $NaNO_3$.

EXAMPLE 20

In this example, the efficacy of the calixarene (compound 10) is tested to extract strontium and sodium from aqueous solutions without nitric acid having variable $NO_3Na$ concentrations (0.5, 1, 2, 4 and 4 M). The same operating mode is followed as in example 15 using an organic phase made up of compound 10 at a concentration of $10^{-2}$ mol/L in NPHE.

Figure 5:
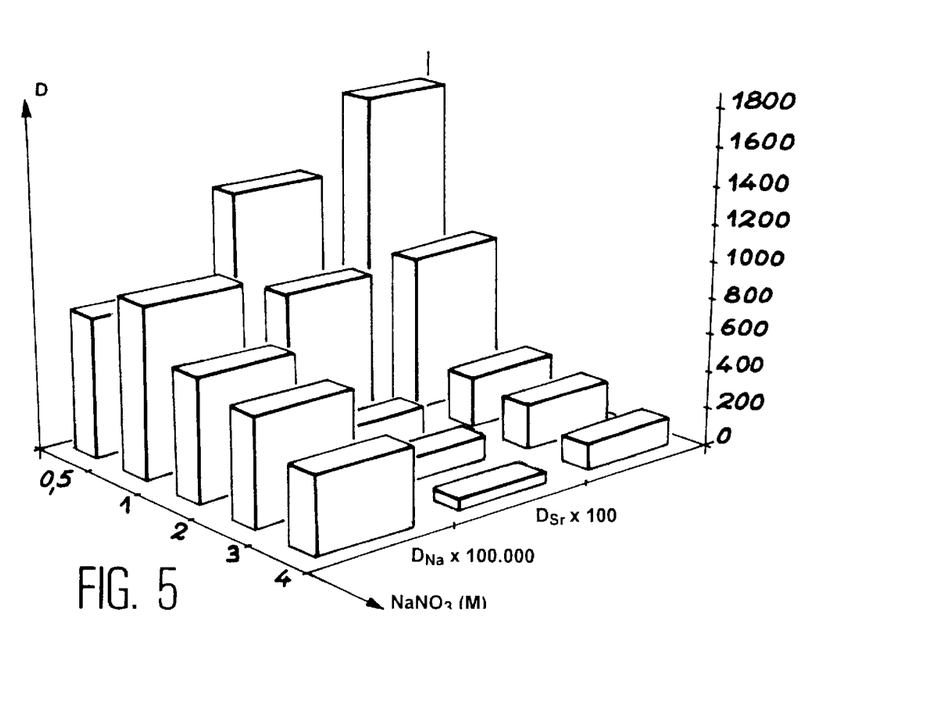
FIG. 5 illustrates the changes in the distribution coefficients $D_{Sr}$ and $D_{Na}$ and in Sr/Na selectivity in relation to the sodium nitrate content of the initial aqueous solution, in the absence of $HNO_3$, in the case of compound 10.

The results obtained are given in FIG. 5 which illustrates the changes in $D_{Sr}$, $D_{Na}$ and Sr/Na selectivity in relation to the concentration of $NaNO_3$.

CITED REFERENCES

[1] WO94/12502.
[2] WO94/24138.
[3] Shinkai, Bull. Chem. Soc. Jpn., 1994, 10499.
[4] Markoxitz JACS, 1989, 111, 81–92.

TABLE 1

| | Example 15 | | | |
|---|---|---|---|---|
| Calixarene in | M(NO$_3$)n 5.10$^{-4}$ M—HNO$_3$ 1M | | | |
| NPHE 10$^{-2}$ M | $^{22}$Na | $^{85}$Sr | $^{137}$Cs | Sr/Na |
| Compound 3 | <10$^{-3}$ | 20 | <10$^{-3}$ | >20000 |
| Compound 8 | <10$^{-3}$ | 6.5 | <10$^{-3}$ | 6500 |
| Compound 9 | <10$^{-3}$ | 30 | <10$^{-3}$ | >30000 |
| Compound 10 | <10$^{-3}$ | 24 | <10$^{-3}$ | >24000 |
| Compound 11 | | Precipitation | | |
| Compound 12 | 6.10$^{-3}$ | 8.3 | 10$^{-2}$ | 1400 |
| Compound 4 | <10$^{-3}$ | 2.9 | <10$^{-3}$ | >2900 |
| Compound 13 | 0.04 | 1.13 | | 28 |

TABLE 2

Example 16

| Calixarene in NPHE $10^{-2}$ M | NaNO$_3$ 4M - HNO$_3$ $10^{-2}$ M | | | |
|---|---|---|---|---|
| | $^{22}$Co | $^{85}$Sr | $^{137}$Cs | $^{152}$Eu |
| Compound 3 | <$10^{-3}$ | 1.5 | $6.10^{-2}$ | <$10^{-3}$ |
| Compound 8 | <$10^{-3}$ | 0.8 | <$10^{-3}$ | <$10^{-3}$ |
| Compound 9 | <$10^{-3}$ | 1.5 | <$10^{-3}$ | $4.10^{-2}$ |
| Compound 10 | <$10^{-3}$ | 1.3 | $9.10^{-3}$ | $9.10^{-2}$ |
| Compound 11 | <$10^{-3}$ | $8.10^{-2}$ | $1,6.10^{-2}$ | <$10^{-3}$ |
| Compound 12 | <$10^{-3}$ | 0.5 | $3.10^{-3}$ | <$10^{-3}$ |

TABLE 3

Example 17

| Calixarene in NPHE $10^{-2}$ M | NaNO$_3$ 4M - HNO$_3$ 1M | | | |
|---|---|---|---|---|
| | $^{60}$Co | $^{85}$Sr | $^{137}$Cs | $^{152}$Eu |
| Compound 3 | <$10^{-3}$ | 5 | 0.1 | <$10^{-3}$ |
| Compound 8 | <$10^{-3}$ | 2.2 | 0.28 | <$10^{-3}$ |
| Compound 9 | <$10^{-3}$ | 0.34 | 0.14 | <$10^{-3}$ |
| Compound 10 | <$10^{-3}$ | 3.8 | 0.27 | <$10^{-3}$ |
| Compound 11 | <$10^{-3}$ | 0.4 | 0.2 | <$10^{-3}$ |
| Compound 12 | <$10^{-3}$ | 1.3 | $3.10^{-2}$ | <$10^{-3}$ |
| Compound 4 | <$10^{-3}$ | 1.8 | <$10^{-3}$ | <$10^{-3}$ |
| Compound 13 | | 0.13 | | |

What is claimed is:

1. Derivative of calixarene having the formula:

(I)

in which:
R$^1$ represents a hydroxyl, alcoxy, aryloxy, arylalcoxy, or cycloalcoxy group, or a group having the formula O(CH$_2$)$_n$[O (CH$_2$)$_p$]$_q$OR$^4$ (II) in which R$^4$ represents a hydrogen atom or an alkyl group, n and p are whole numbers ranging from 1 to 6, and q equals 0 or is a whole number from 1 to 6, R$^2$ and R$^3$, which identical different, represent an alkyl, cycloalkyl or aryl group or a group having the formula: O(CH$_2$)$_n$[O(CH$_2$)$_p$]$_q$OR$^4$ (II) in which R$^4$, n, p and q are such as defined above, or R$^2$ and R$^3$, together with the nitrogen atom to which they are bound, form a heterocyclic group chosen from among the piperidyl, pyrrolidinyl, morpholinyl, thiomorpholinyl, tetrahydropyridyl, imidazolidinyl, indolinyl, tetrahydroquinolyl and perhydroindolyl groups, and m is a whole number ranging from 6 to 8.

2. Calixarene derivative according to claim 1, in which R$^1$ is an alcoxy or arylalcoxy group.

3. Calixarene derivative according to claim 2, in which the alcoxy group is the pentoxy or octoxy group.

4. Calixarene derivative according to claim 2, in which the arylalcoxy group is the benzyloxy group.

5. Calixarene derivative according to claim 1, in which R$^2$ and R$^3$ are alkyl groups.

6. Calixarene derivative according to claim 1, in which m equals 6 or 8.

7. Calixarene derivative chosen from among:
5,11,17,23,29,35,41,47-octabenzyloxy-49,50,51,52,53,54,55,56-octakis[N,N-diethylamino-carbonyl)methoxy]calix[8]arene,
5,11,17,23,29,35,41,47-octamethoxy-49,50,51,52,53,54,55,56-octakis[N,N-diethylamino-carbonyl)methoxy]calix[8]arene,
5,11,17,23,29,35-hexamethoxy-37,38,39,40,41,42-hexakis[N,N-diethylaminocarbonyl)methoxy]-calix[6]arene,
5,11,17,23,29,35-hexabenzyloxy-37,38,39,40,41,42-hexakis[N,N-diethylamino-carbonyl)methoxy]calix[6]arene,
5,11,17,23,29,35,41,47-octakis(1,1-dimethylethyl)-49,50,51,52,53,54,55,56-octakis[N,N-diethylamino-carbonyl)methoxy]calix[8]arene,
49,50,51,52,53,54,55,56-octakis[N,N-diethylamino-carbonyl)methoxy]calix[8]arene,
5,11,17,23,29,35,41,47-octapentoxy-49,50,51,52,53,54,55,56-octakis[N,N-diethylamino-carbonyl)methoxy]calix[8]arene,
5,11,17,23,29,35,41,47-octaoctoxy-49,50,51,52,53,54,55,56-octakis[N,N-diethylamino-carbonyl)methoxy]calix[8]arene,
5,11,17,23,29,35,41,47-octahydroxy-49,50,51,52,53,54,55,56-octakis[N,N-diethylamino-carbonyl)methoxy]calix[8]arene,
5,11,17,23,29,35,41-heptakis (1,1-dimethylethyl)-43,44,45,46,47,48,49-heptakis (N,N-diethylamino-carbonyl)methoxy]calix[8]arene, and
5,11,17,23,29,35-hexahydroxy-37,38,39,40,41,42-hexakis [N,N-diethylaminocarbonyl)methoxy]calix(6) arene.

8. Method for preparing a calixarene derivative having the formula:

(I)

in which:
R$^1$ represents a hydrogen atom, an alkyl group or a benzyloxy group, R² and R³, which may identical or different, represent an alkyl, cycloalkyl or aryl group or a group having the formula: $O(CH_2)_n[O(CH_2)_p]_qOR^4$ (II) in which R⁴, n, p and q are such as defined above, or

R² and R³, together with the nitrogen atom to which they are bound, form a heterocyclic group chosen from among the piperidyl, pyrrolidinyl, morpholinyl, thiomorpholinyl, tetrahydropyridyl, imidazolidinyl, indolinyl, tetrahydroquinolyl and perhydroindolyl groups, and m is a whole number ranging from 6 to 8, which comprises the reaction of a calixarene having the formula:

(III)

in which R¹ and m are such as defined above, with a chloroacetamide having the formula:

(IV)

in which R² and R³ are such as defined above.

9. Method for preparing a calixarene derivative having the formula:

(I)

in which:
R¹ represents an alcoxy group,
R² and R³, which may identical or different, represent an alkyl, cycloalkyl or aryl group or a group having the formula: $O(CH_2)_n[O(CH_2)_p]_qOR^4$ (II) in which R⁴, n, p and q are such as defined above, or R² and R³, together with the nitrogen atom to which they are bound, form a heterocyclic group chosen from among the piperidyl, pyrrolidinyl, morpholinyl, thiomorpholinyl, tetrahydropyridyl, imidazolidinyl, indolinyl, tetrahydroquinolyl and perhydroindolyl groups, and m is a whole number ranging from 6 to 8, which comprises the following steps:

a) reaction of a calixarene having the formula:

(V)

in which m is such as defined above, with a chloroacetamide having the formula:

(IV)

in which R² and R³ are such as defined above, in order to obtain the derivative having the formula:

(VI)

in which R² and R³ are such as defined above, b) reaction of the derivative of formula (VI) with Pd(OH₂) to obtain the calixarene having the formula:

(VII)

c) reaction of the calixarene of formula VII with a halogenated derivative of formula $R^5X$ in which $R^5$ represents an alkyl group and X is a halogen atom, to obtain the calixarene derivative of formula (I) in which $R^1$ represents the alcoxy group $OR^5$.

10. Met hod for preparing a calixarene derivative having the formula:

(III)

in which $R^1$ represents the benzyloxy group and m equals 6 or 8, by condensation reaction of p-benzyloxyphenol having the formula:

(VIII)

to obtain a mixture of calix[6]arene, calix[7]arene and calix[8]arene of formula (III), and separation of the calixarene of formula (III) in which m=6 or 8.

11. Method for extracting strontium present in an aqueous solution, which consists of contacting the aqueous solution with an immiscible phase containing at least one calixarene derivative having the formula:

(I)

in which:

$R^1$ represent a hydrogen atom, an alkyl, alcoxy, aryl, aryloxy, arylalkyl, arylalcoxy, cycloalkyl or cycloalcoxy group, or a group having the formula: $O(CH_2)_n[O(CH_2)_p]_qOR^4$ (II) in which $R^4$ represents a hydrogen atom or an alkyl group, n and p are whole numbers ranging from 1 to 6, and q equals 0 or is a whole number from 1 to 6, $R^2$ and $R^3$, which may identical or different, 5 represent an alkyl, cycloalkyl or aryl a group having the formula: $O(CH_2)_n[O(CH_2)_p]_qOR^4$ (II) in which $R^4$, n, p and q are such as defined above, or $R^2$ and $R^3$, together with the nitrogen atom to which they are bound, form a heterocyclic group chosen from among the piperidyl, pyrrolidinyl, morpholinyl, thiomorpholinyl, tetrahydropyridyl, imidazolidinyl, indolinyl, tetrahydroquinolyl and perhydroindolyl groups, and m is a whole number ranging from 6 to 8, to extract strontium in the immiscible phase.

12. Method according to claim 11, in which the aqueous solution is a nitric solution containing from 1 to 4 mol/l nitric acid, or a saline solution having a sodium nitrate concentration of 1 to 4 mol/L.

13. Method according to claim 11, in which the immiscible phase is a solution of the derivative of calixarene of formula (I) in an organic solvent.

14. Method according to claim 13, in which the organic solvent is a nitrophenyl-alkylether.

* * * * *